(12) United States Patent
Van Schie et al.

(10) Patent No.: US 6,974,471 B2
(45) Date of Patent: Dec. 13, 2005

(54) PROSTHESES FOR CURVED LUMENS

(75) Inventors: Gregory Paul Van Schie, Western Australia (AU); David Ernest Hartley, Western Australia (AU)

(73) Assignees: Cook Incorporated, Bloomington, IL (US); William A. Cook Australia PTY LTD, Queensland (AU)

( * ) Notice: Subject to any disclaimer, the term of this patent is extended or adjusted under 35 U.S.C. 154(b) by 80 days.

(21) Appl. No.: 10/280,486

(22) Filed: Oct. 25, 2002

(65) Prior Publication Data

US 2003/0088305 A1 May 8, 2003

(30) Foreign Application Priority Data

Oct. 26, 2001 (AU) .............................................. PR8473

(51) Int. Cl.[7] .................................................. A61F 2/06
(52) U.S. Cl. ...................................... 623/1.12; 623/1.13
(58) Field of Search .............................. 623/1.12–1.16, 623/1.2, 2.36

(56) References Cited

U.S. PATENT DOCUMENTS

| | | | |
|---|---|---|---|
| 5,876,419 A | | 3/1999 | Carpenter et al. |
| 5,916,147 A | * | 6/1999 | Boury .......................... 600/146 |
| 6,071,307 A | * | 6/2000 | Rhee et al. ................. 623/1.13 |
| 6,402,781 B1 | * | 6/2002 | Langberg et al. ........... 623/2.36 |
| 6,602,288 B1 | * | 8/2003 | Cosgrove et al. ........... 623/2.36 |
| 2002/0013617 A1 | * | 1/2002 | Matsutani et al. .......... 623/1.15 |
| 2002/0156522 A1 | * | 10/2002 | Ivancev et al. ............. 623/1.13 |
| 2003/0078561 A1 | * | 4/2003 | Gambale et al. ............ 604/508 |
| 2003/0097170 A1 | * | 5/2003 | Friedrich et al. ........... 623/1.13 |
| 2003/0097171 A1 | * | 5/2003 | Elliott ........................ 623/1.15 |

FOREIGN PATENT DOCUMENTS

| EP | 1036551 | 9/2000 |
|---|---|---|
| EP | 1177779 | 2/2002 |
| WO | 0239925 | 5/2002 |

\* cited by examiner

*Primary Examiner*—Suzette J-J Gherbi (57) ABSTRACT

A prosthetic device (1) adapted for the carriage of fluids therethrough within a human or animal body and to be placed in or replace a curved lumen. The prosthetic device has a control arrangement to control the length of one side with respect to the other side so that the device can be curved insitu to fit the curved lumen. The control arrangement can be an expansion restriction arrangement or a length reduction arrangement. The prosthesis can be stented or unstented and be formed from a tubular or corrugated material.

12 Claims, 8 Drawing Sheets

PROSTHESES FOR CURVED LUMENS

CROSS-REFERENCE TO RELATED APPLICATIONS

This application claims priority of Australian Provisional Application Serial No. PR 8473 filed Oct. 26, 2001.

TECHNICAL FIELD

This invention relates to prostheses and in particular to prostheses suitable for curved lumens of the body.

BACKGROUND OF THE INVENTION

In general the invention will be discussed in relation to the placement of prostheses in the aorta in the region known as the thoracic arch where the aorta leaves the heart and curves over in approximately a semi-circle to the descending aorta and then into the abdominal aorta and then into the lower limbs via the iliac arteries. The invention is, however, not so restricted and can relate to placement of prostheses within or in place of lumens in any portion of a human or animal body.

Aortic aneurysms can occur high up in the thoracic aorta and in this region the aorta is curved and placement of a substantially cylindrical prosthesis in such a curved region can cause problems. The upper end of the prosthesis may not attain close apposition to the vessel wall. This can result in the lumen of the prosthesis being closed off or reduced in lumen diameter. Kinks can also occur along the length of the prosthesis and these can cause problems with restriction of flow in the lumen.

SUMMARY OF THE INVENTION

It is the object of this invention therefore to provide an endoluminal prosthesis suitable for placement in curved lumens such as the thoracic arch by making it more conforming.

Throughout this specification with respect to discussion of the thoracic arch of a patient the term distal with respect to a prosthesis is the end of the prosthesis furthest away in the direction of blood flow from the heart and the term proximal means the end of the prosthesis nearest to the heart.

In one form the invention may be said to reside in a flexible tubular prosthetic device for the carriage of fluids therethrough within a human or animal body and for placement in or replacement of a curved lumen, the prosthetic device having diametrically opposed first and second sides and a control arrangement to control the length of the first longitudinal side with respect to the second longitudinal side, whereby the device can be curved insitu to fit the curved lumen.

In one form the control arrangement to control the length of the first longitudinal side may be an expansion restriction arrangement to restrict expansion of at least part of the first side. Alternatively, the control arrangement may be an arrangement to reduce at least part of the length of the first side.

The prosthetic device may be a stented prosthesis or an unstented prosthesis.

The expansion restriction arrangement can be stitching or stapling on the first side so that the amount of expansion which can occur on the first side is restricted.

The prosthetic device can have transverse corrugations defining alternate ridges and valleys along at least part of the length of the prosthetic device and thereby providing a device which is longitudinally extendable and the expansion restriction arrangement may prevent expansion of at least some of the corrugations on the first side.

In one form there can be stitching or stapling of some of the corrugations.

Each corrugation in a portion of the device, alternate corrugations or in one in three corrugations can be stitched or stapled for instance.

In a preferred embodiment the expansion restriction arrangement comprises stitching or stapling together of adjacent corrugations of some of the corrugations on the first longitudinal side, whereby upon stretching of the flexible tubular prosthetic device, the second longitudinal side can extend more than the first longitudinal side thereby forming a curve in the flexible tubular prosthetic device.

In an alternative form, the invention is said to reside in an endoluminal prosthesis for placement in a curved lumen, the prosthesis having a biocompatible graft material tube and having a length reduction arrangement on one longitudinal side of the tube, whereby upon deployment within the lumen, the length of the one longitudinal side of the prosthesis can be reduced with respect to an opposite longitudinal side of the prosthesis to cause the prosthesis to curve to better fit the walls of the curved lumen.

Generally, it can be seen that the prosthesis is substantially cylindrical or potentially cylindrical when it is installed or deployed but during the deployment process the graft is deliberately curved with respect to a longitudinal axis of the prosthesis to enable to better fit the lumen.

By potentially cylindrical is meant that the prosthesis when it is at the stage of deployment, it can be radially compressed so that it can be carried in the deployment device to the deployment site but would be cylindrical if allowed to open not under the influence of the length reduction or length restriction arrangement.

In one form, the graft material tube can have a plurality of stents mounted along the length of the graft tube.

In one form of the invention, the stents can be balloon expanded mesh metal stents.

In an alternative form of the invention, the stents can be self expanding stents such as zig zag stents or z stents.

In a preferred form of the invention, the stents can be spaced apart along the length of the graft material tube and during the activation of the length reduction arrangement, the stents on one side of the graft move closer together while they stay substantially the same distance apart on the other side of the prosthesis.

The stents can overlap to provide the length reduction on one side of the prosthesis.

In one form of the invention, the length reduction arrangement comprises a length of elastic material positioned longitudinally along part or all of the length of the graft material tube. When the prosthesis is installed in a deployment device and transported in the deployment device, the elastic material is stretched, but upon release from the deployment device the elastic material contracts in length to reduce the length of one side of the prosthesis with respect to the other side and hence causes the graft to curve. The elastic material can be a silicone rubber or similar material. Alternatively, the elastic material can be a shape memory metal which when released from the deployment device tends to reduce in length. This may for instance be a longitudinally extending zig zag or z stent which has been stretched to be substantially straight for deployment but resumes its zig zag nature and hence reduces in length during release from deployment.

In another form, the length reduction arrangement can be a stainless steel spring extending down at least one part of the side of the prosthesis and in a similar manner to the embodiment discussed immediately above would be stretched for transport in the deployment device and reduces in length when released from the deployment device.

In a further alternative form, the length reduction arrangement comprises a series of sutures or alternative forms of cords or strings fitted to the prosthesis tube at one or more places along the length of the tube which reduces the length of the graft as the diameter increases upon expansion after release. This can be provided by having the suture or string being fixed to two positions on the surface of the graft material with part of its length extending circumferentially on the surface of the graft and part longitudinally. Hence during the expansion of the prosthesis upon deployment as the circumference of the prosthesis increases, the length of the longitudinal portion of the suture must reduce, which draws that part of the prosthesis closer to the part of the graft where the circumferential portion of the suture is situated. Generally therefore, as the diameter of the graft increases upon expansion, the longitudinal length on one side decreases.

In an alternative arrangement of the length reduction arrangement, there can be an anchor wire fitted into the length of the graft material tube on one side with the anchor wire joined to the proximal end of the prosthesis with a slip knot adapted to release the anchor wire when desired. To cause the prosthesis to curve after deployment the anchor wire can be pulled to reduce the length of one side of the graft. When the correct amount of curve has been achieved, which can be observed by angiography or other techniques, the anchor wire can be released by releasing the slip knot with a trigger wire or other release technique. The anchor wire can have a small bulb at its end of a type referred to as an olive to provide an engagement abutment for the slip knot.

BRIEF DESCRIPTION OF THE DRAWING

This then generally described the invention but to assist with understanding reference will now be made to the accompanying drawings which show preferred embodiments of the invention.
In the drawings.

DETAILED DESCRIPTION

In all of the drawings to assist with clarity of depiction of the invention the curved lumen such as a thoracic aorta is not shown.

Figure 1:
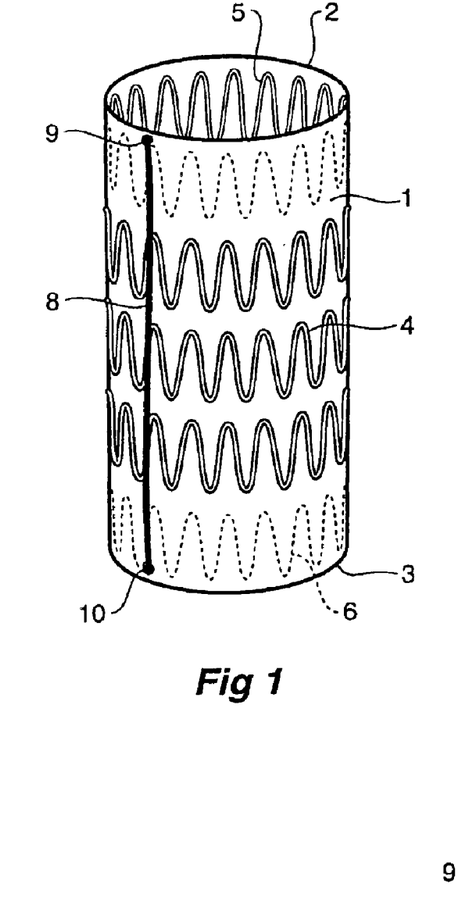
FIG. 1 shows a first embodiment of the present invention incorporating an elastic material to provide a reduction in the length of one part of the prosthesis with respect to another.
Figure 2:
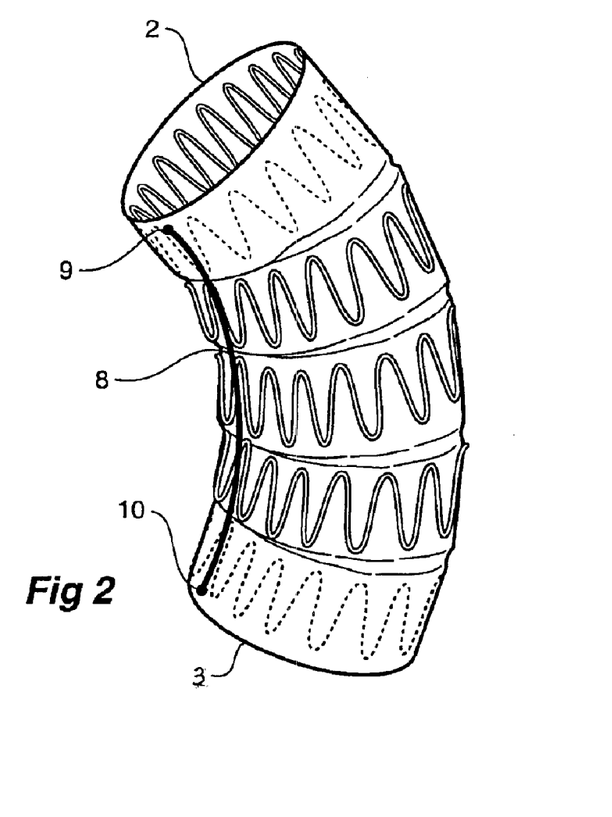
FIG. 2 shows the graft shown in FIG. 1 after deployment and release of the prosthesis so that it may take up a curve.

Now looking more closely at the drawings and in particular the embodiment shown in FIGS. 1 and 2 it will be seen that the prosthesis comprises a graft material tube 1 which is substantially cylindrical. The graft material tube has a proximal end 2 and a distal end 3. The graft has a number of self expanding zig zag or well-known Gianturco z stents 4 positioned at intervals along the length of the tube and providing the force necessary to open the graft out to the walls of the aorta when deployed. In this embodiment the stents 5 and 6 at the distal and proximal ends respectively are inside the graft and the other intermediate stents are on the outside of the graft.

In this embodiment the length reduction arrangement is an elastic material 8 such as a silicone rubber or similar material which is fastened at 9 at the proximal end 2 of the prosthesis and joined at 10 near the distal end 3 of the prosthesis. The length reduction arrangement can also comprise a shape memory metal such as Nitinol, a nickel titanium alloy, which is heat set in a curved configuration.

Upon deployment as shown in FIG. 2, the ends of the graft are released from a deployment device (not shown) and the elastic material 8 takes up its shortened rest position so that the points 9 and 10 move closer together which causes the graft to form a curved shape.

It may be noted that the elastic material may not extend the entire length of the prosthesis but may be used on only part of the length of the prosthesis so that the prosthesis when placed may have a curved portion and a straight portion.

In the embodiment shown in FIGS. 3 to 6, the graft material tube 20 again has a number of zig zag or z stents 21, 22 and 23 spaced at intervals along its length.

Figure 3:
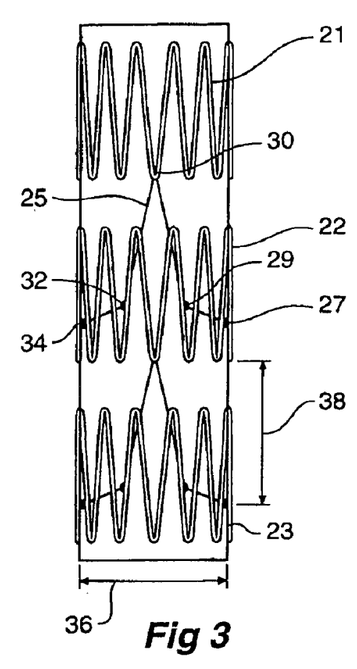
FIG. 3 shows an alternative embodiment of the prosthesis of the present invention.
Figure 4:
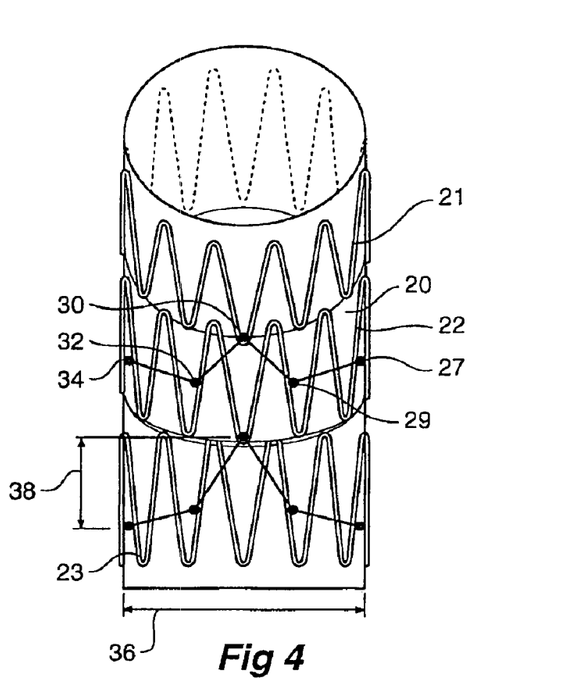
FIG. 4 shows a view of the embodiment shown in FIG. 3 after expansion.
Figure 5:
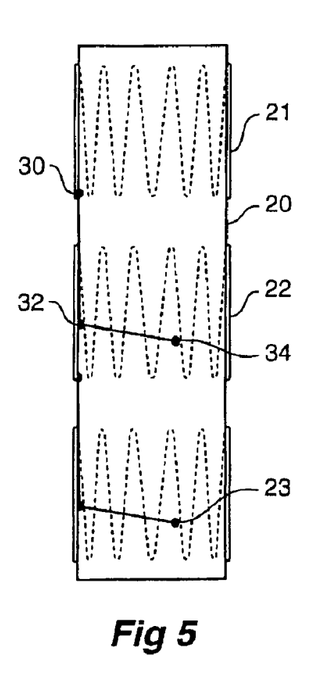
FIG. 5 shows a cross sectional view of the embodiment shown in FIG. 3.
Figure 6:
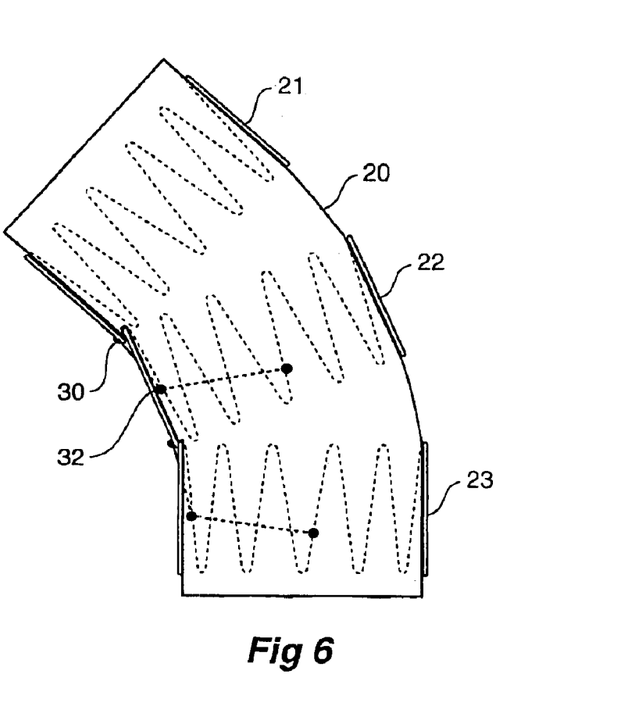
FIG. 6 shows a cross sectional view of the embodiment shown in FIG. 3 in the expanded condition.

In this embodiment, FIGS. 3 and 5 show the graft in a compressed state as it would be during deployment and FIGS. 4 and 6 show the graft after deployment when the self expanding stents 21, 22 and 23 have expanded so that the graft engages the wall of the aorta into which it is deployed.

To cause the curving as shown in FIGS. 4 and 6, a length of suture material 25 is fastened at 27 to the graft material or one of the stents and is then passed circumferentially around the prosthesis to a point 29 where it is inserted through the graft material and then extends longitudinally along the prosthesis to a point 30 where it is passed through a curve of one of the apices of the zig zag portions of the stent 21. The suture material then passes down to point 32 substantially adjacent to the point 29 and then passes around the circumference of the stent to a point 34 substantially in line with the point 27.

The distance between the points 27 and 34 is shown by the arrow 36 and the distance between the points 29 and 30 is shown by the arrow 38.

As the graft expands as shown in FIG. 4 and FIG. 6 when the graft is deployed and released from the deployment device, the circumference of the prosthesis increases by expansion of the z stents and hence the distance 36 as shown in FIG. 4 increases and the distance 38 therefore decreases which pulls the point 30 down towards the points 29 and 32. This can cause the proximal end of the stent 21 to overlap the distal end of the stent 22 on the side where the length is being reduced.

It will be noted that on the opposite side of the prosthesis as particularly can be seen in FIG. 6, the spacing of the stents 21, 22 and 23 remain substantially the same.

It will be seen that by this arrangement the distance between one or more stents on one side of the prosthesis can be reduced thereby inducing a curve in the prosthesis or part of the length of the prosthesis.

Figure 7:
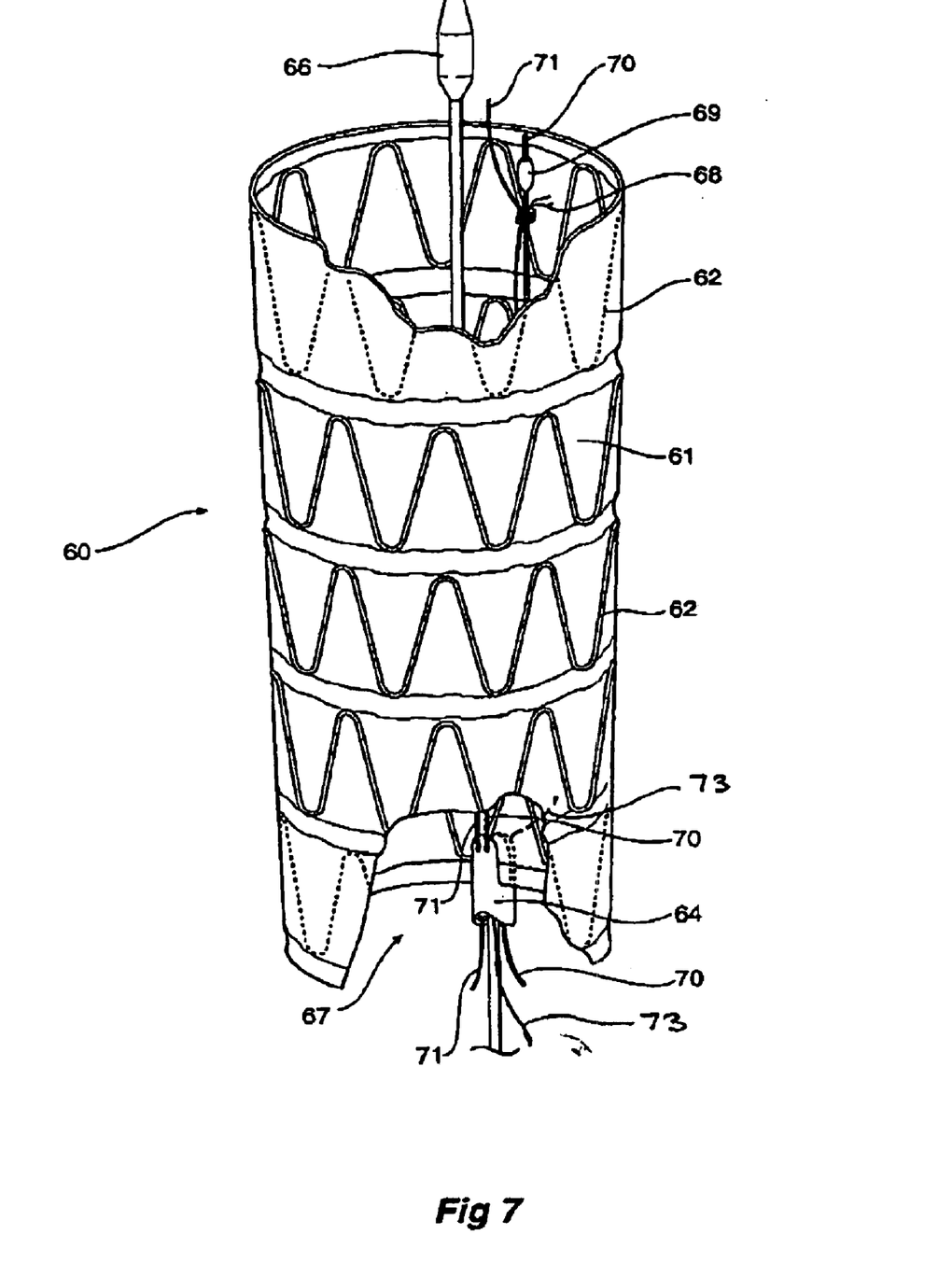
FIG. 7 shows an alternative form of the prosthesis according to the present invention using a self-expanding stent system and an anchor wire curving system.
Figure 8:
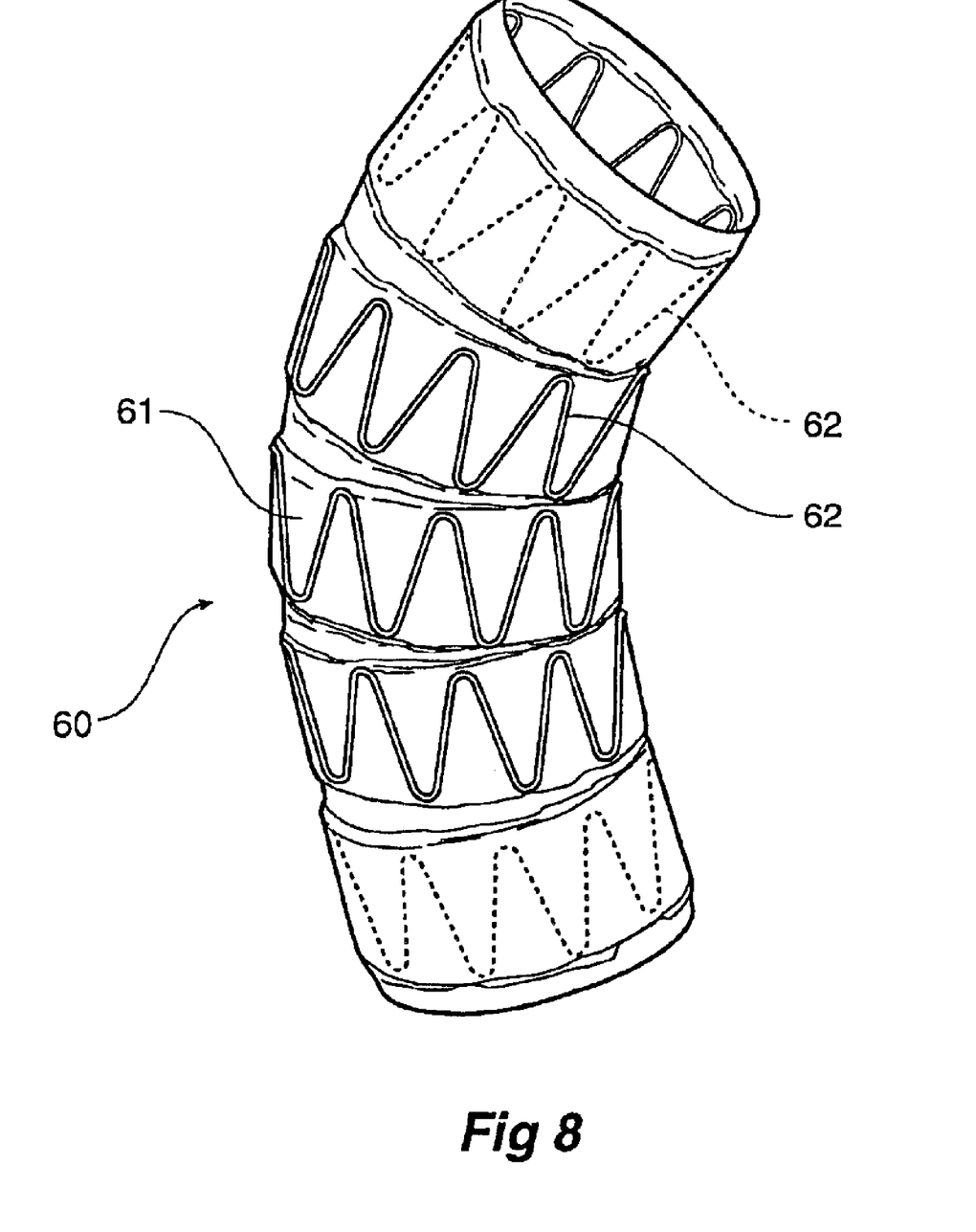
FIG. 8 shows the prosthesis of FIG. 7 in the deployed and curved position.

In an alternative embodiment shown in FIGS. 7 and 8, a prosthesis 60 has a graft material tube 61 and a number of self expanding stents 62. A deployment device comprises a catheter 64 with at the proximal end of the catheter 64 a nose cone 66. The distal end of the prosthesis is joined to the deployment device at 67 by a releasable attachment arrangement. An anchor wire 70 exits the catheter 64 and passes up inside the prosthesis and is joined at the proximal end of the graft by a slip knot 68 which engages against an olive 69 on the end of the anchor wire 70 which can be released by trigger wire 71.

When the graft is deployed and the self expanding stents are allowed to expand by removal of a sheath (not shown) and a release mechanism (not shown) the anchor wire 70 can be pulled to reduce the length of that side of the prosthesis with respect to the other to place the prosthesis into a curved configuration as shown in FIG. 8. Expansion of the stents 62 may be done sequentially by only partial removal of the sheath to below the position of each stent with a part of the curving process by the use of tension on the anchor wire 70 after each expansion. After deployment and curving the anchor wire 70 can be released by pulling on the trigger wire 71, which releases the slip knot 68 so that the anchor wire can be withdrawn as far as the deployment catheter 64. The attachment arrangement 67 can then be released by withdrawal of a further trigger wire 73 so that the deployment device can be withdrawn from the patient leaving the prosthesis in the curved shape as shown in FIG. 8.

In an alternative arrangement the trigger wires 71 and 73 can be the same wire which is partially withdrawn to release the slip knot 68 and subsequently fully withdrawn to release the proximal attachment arrangement 67.

Figure 9:
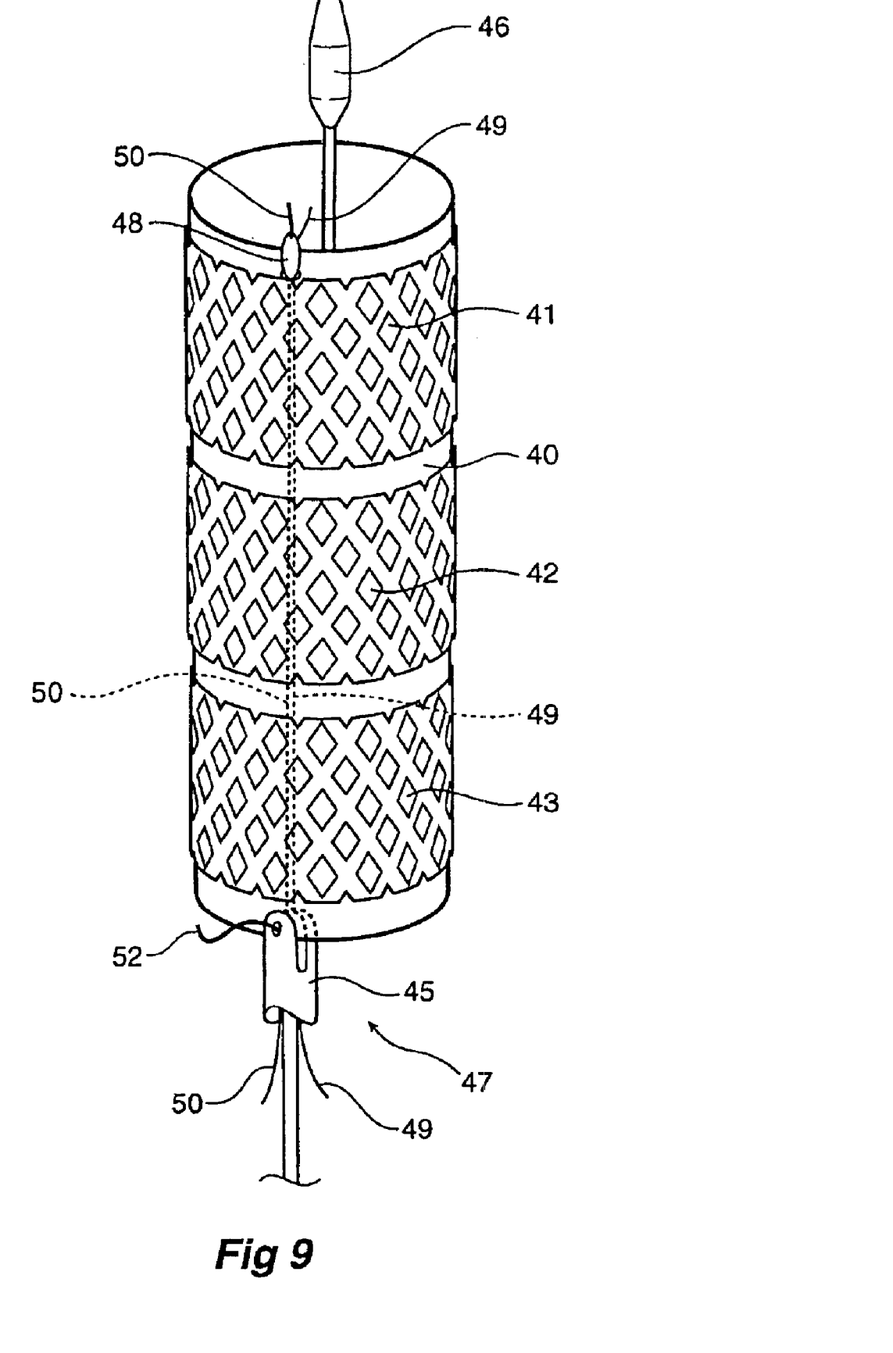
FIG. 9 shows an alternative form of the prosthesis according to the present invention using a balloon expanded stent system and an anchor wire curving system.
Figure 10:
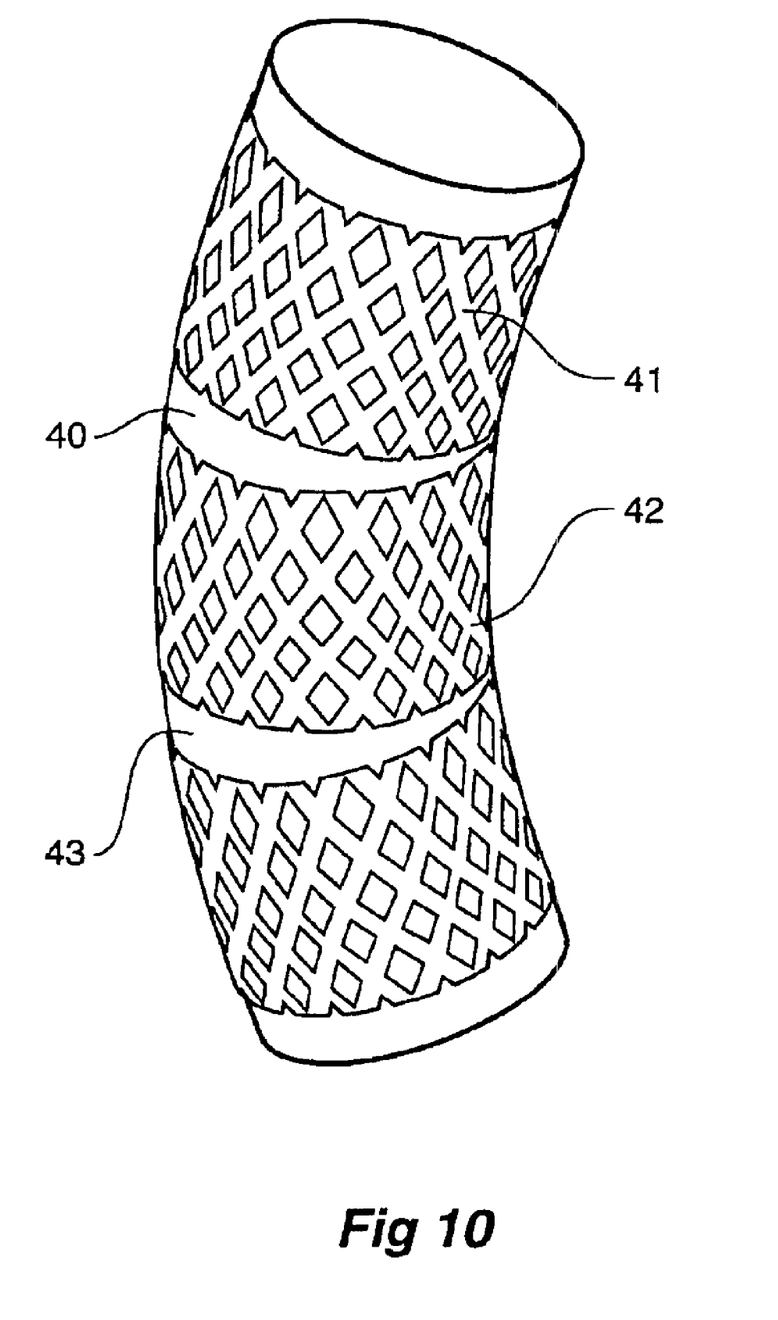
FIG. 10 shows the prosthesis of FIG. 9 in the deployed and curved position.
Figure 11:
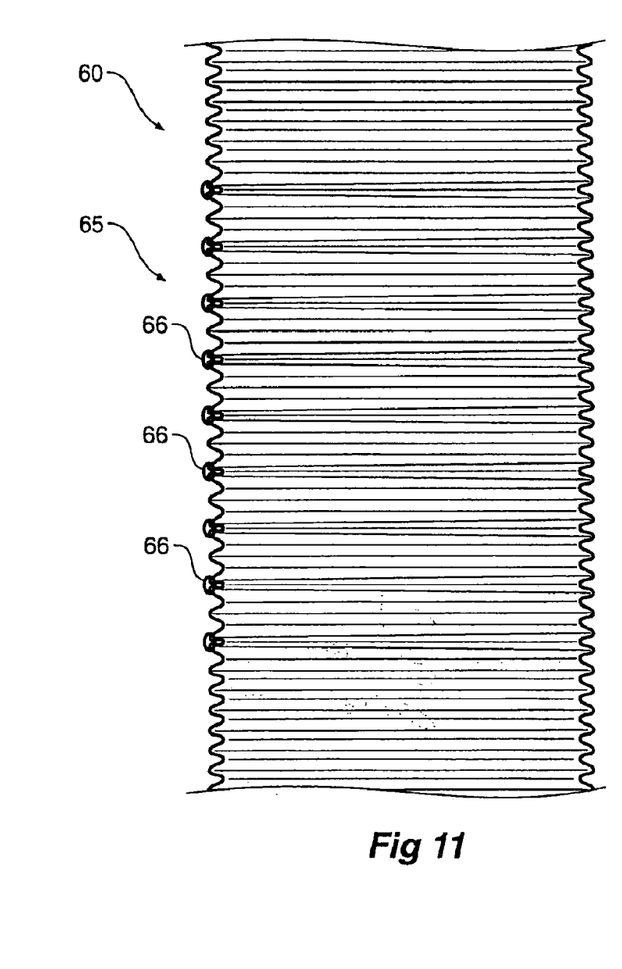
FIG. 11 shows another alternate embodiment of the prostheses of the present invention.
Figure 12:
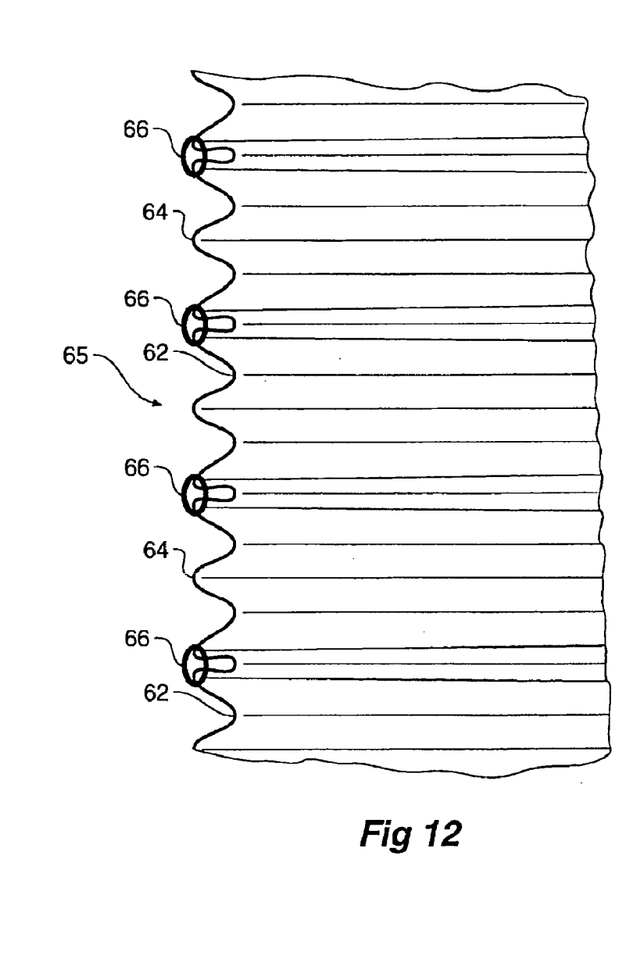
FIG. 12 shows a detail of the embodiment of FIG. 11.
Figure 13:
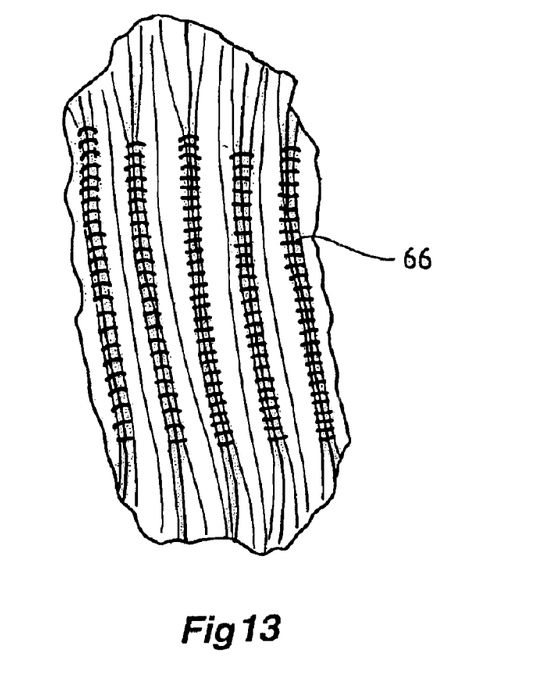
FIG. 13 shows further detail of the embodiment of FIG. 11.

In an alternative embodiment shown in FIGS. 9 and 10, a prosthesis has a graft material tube 40 and three balloon expandable mesh stents 41, 42 and 43. A deployment device comprises a catheter 45 with at the proximal end of the catheter 45 a nose cone 46. The distal end of the prosthesis is joined to the deployment device at 47 by a releasable attachment arrangement. An anchor wire 50 exits the catheter 45 and passes up the prosthesis and is joined at the proximal end of the graft by a slip knot 48, which can be released by trigger wire 49.

When the graft is deployed and the expanding stents expanded by balloon means (not shown), the anchor wire 50 can be pulled to reduce the length of that side of the prosthesis with respect to the other as shown in FIG. 10. Expansion of the stents 41, 42 and 43 may be done sequentially by inflation of a balloon (not shown) in the position of each stent with a part of the curving process by the use of tension on the anchor wire 50 after each expansion. After deployment and curving, the anchor wire 50 can be released by pulling on the trigger wire 49, which releases the slip knot 48 so that the anchor wire can be withdrawn. The attachment arrangement 47 can then be released by withdrawal of a further trigger wire 52 so that the deployment device can be withdrawn from the patient leaving the prosthesis in the curved shape as shown in FIG. 10.

In an alternative arrangement, the trigger wires 49 and 52 can be the same wire which is partially withdrawn to release the slip knot 48 and subsequently fully withdrawn to release the proximal attachment arrangement 47.

Now looking at the embodiment shown in FIGS. 11 to 14, there is shown an alternative embodiment of the prosthetic device. This device is a transversely corrugated tube of biocompatible material. It can be used to entirely replace a portion of vasculature, for instance, or is deployed endoluminally to reinforce a portion of vasculature.

The corrugated prosthetic device is usually used without stents and hence when it is used for a curved portion of a lumen it can tend to kink with attendant dangers of a vessel closing. The present invention proposes an arrangement by which the danger of closing is reduced.

Figure 14:
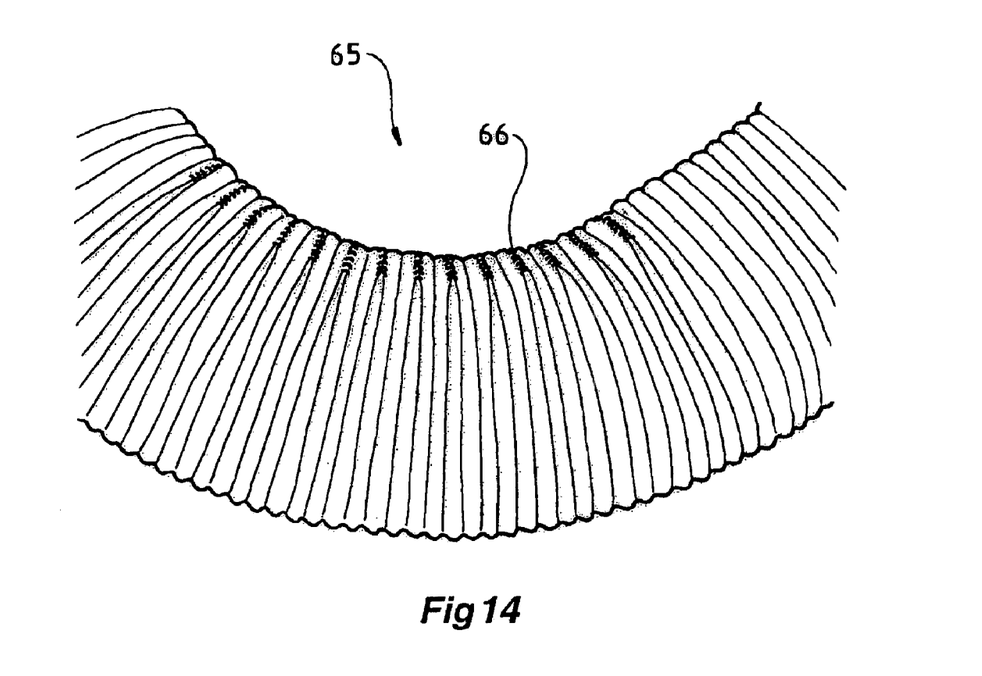
FIG. 14 shows the embodiment of FIG. 11 after curving.

In the drawings, prosthesis 60 is formed from a biocompatible material and has transverse corrugations defined by troughs 62 and ridges 64. This provides a prosthesis which is extensible, but when curved can buckle or kink. Hence, according to this invention, some of the ridges along a longitudinal side 65 are stitched up to form stitches 66 which in turn form the expansion restriction arrangement to limit the amount of extension possible for these ridges on that side. When the prosthesis is curved as shown in FIG. 14, the stitching 66 is used on the inner portion of the curve. The outer portion of the curve 68 can expand as there is no expansion restriction means.

By this arrangement when the prosthesis is inflated, under blood pressure for instance, the prosthesis takes up a curved configuration with less chance of buckling or kinking and closing off.

It will be realized that although the various embodiments have been shown with particular forms of prostheses the various embodiments of the invention can be used with any of the forms of prostheses. Other forms of prostheses and graft material and stented and unstented material can also be used.

Throughout this specification various indications have been given as to the scope of the invention but the invention is not limited in any one of these but may reside in two or more of these combined together. The examples are given for illustration only and not for limitation.

Throughout this specification unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A flexible tubular prosthetic device for the carriage of fluids therethrough within a human or animal body and for placement in or replacement of a curved lumen, the prosthetic device comprising a graft material tube and a plurality of stents, the tube having diametrically opposed first and second longitudinal sides and a control arrangement to control the length of the first longitudinal side with respect to the second longitudinal side so that the device can be curved insitu to fit the curved lumen, the control arrangement comprising an expansion restriction arrangement capable of restricting expansion of at least part of the first side wherein the expansion restriction arrangement is stitching or stapling on the first side so that the amount of expansion which can occur on the first side is restricted.

2. A flexible tubular prosthetic device as in claim 1 wherein the prosthetic device has transverse corrugations defining alternate ridges and valleys along at least part of the length of the prosthetic device and thereby providing a device which is longitudinally extendable and wherein the expansion restriction arrangement prevents expansion of at least some of the corrugations on the first side.

3. A flexible tubular prosthetic device as in claim 2 wherein the expansion restriction arrangement comprises stitching or stapling together of adjacent corrugations of some of the corrugations on the first longitudinal side, whereby upon stretching of the flexible tubular prosthetic device, the second longitudinal side can extend more than the first longitudinal side thereby forming a curve in the flexible tubular prosthetic device.

4. An endoluminal prosthesis as in claim 1 wherein the stents are spaced apart along the length of the graft material tube and wherein during the activation of the length reduction arrangement, the stents on one side of the graft material tube move closer together while they stay substantially the same distance apart on the other side of the graft material tube.

5. An endoluminal prosthesis for placement in a curved lumen, the prosthesis having a biocompatible graft material tube and having a length reduction arrangement on one longitudinal side of the tube so that upon deployment within the lumen, the length of the one longitudinal side of the prosthesis can be reduced with respect to an opposite longitudinal side of the prosthesis to cause the prosthesis to curve insitu to better fit the walls of the curved lumen, wherein the length reduction arrangement comprises a series of sutures or alternative forms of cords or strings fitted to the prosthesis tube at one or more places along the length of the tube which reduces the length of the graft as the diameter increases upon expansion after release of the prosthesis from a diametrically contracted position, each suture or string being fixed to two positions on the surface of the graft material with part of its length extending circumferentially on the surface of the graft and part longitudinally, whereby during expansion of the prosthesis upon deployment as the circumference of the prosthesis increases, the length of the longitudinal portion of the suture reduces draws that part of the prosthesis closer to the part of the graft where the circumferential portion of the suture is situated.

6. An endoluminal prosthesis for placement in a curved lumen, the prosthesis having a biocompatible graft material tube and having a length reduction arrangement on one longitudinal side of the tube so that upon deployment within the lumen, the length of the one longitudinal side of the prosthesis can be reduced with respect to an opposite longitudinal side of the prosthesis to cause the prosthesis to curve insitu to better fit the walls of the curved lumen, wherein the length reduction arrangement comprises an anchor wire fitted into the length of the graft material tube on one side with the anchor wire joined to the proximal end of the prosthesis with a slip knot to release the anchor wire when desired, whereby the prosthesis curves after deployment wherein the anchor wire is pulled to reduce the length of one side of the graft.

7. A flexible tubular prosthetic device for the carriage of fluids therethrough within a human or animal body and for placement in or replacement of a curved lumen, the prosthetic device comprising a graft material tube, the tube having diametrically opposed first and second longitudinal sides and transverse corrugations defining alternate ridges and valleys along at least part of the length of the prosthetic device and thereby providing a device which is longitudinally extendable, the prosthetic device also having an expansion restriction arrangement which prevents expansion of at least some of the corrugations on the first side, whereby the device can be curved insitu to fit the curved lumen.

8. A flexible tubular prosthetic device as in claim 7 wherein the expansion restriction arrangement is stitching or stapling of some of the corrugations.

9. A flexible tubular prosthetic device as in claim 7 wherein the expansion restriction arrangement comprises stitching or stapling together of adjacent corrugations of some of the corrugations on the first longitudinal side, whereby upon stretching of the flexible tubular prosthetic device, the second longitudinal side can extend more than the first longitudinal side thereby forming a curve in the flexible tubular prosthetic device.

10. A flexible tubular prosthetic device as in claim 7 wherein the prosthetic device is a stented prosthesis.

11. An endoluminal prosthesis as in claim 10 wherein the stents are self-expanding stents.

12. A flexible tubular prosthetic device as in claim 7 whrerin the prosthetic device is an unstented prosthesis.

* * * * *